(12) United States Patent
Stuart et al.

(10) Patent No.: US 11,007,194 B2
(45) Date of Patent: May 18, 2021

(54) METHOD OF TREATING A PROLIFERATIVE DISEASE

(71) Applicant: Array BioPharma Inc., Boulder, CO (US)

(72) Inventors: Darrin Stuart, Pleasant Hill, CA (US); Meghna Das Thakur, Berkeley, CA (US)

(73) Assignee: Array BioPharma Inc., Boulder, CO (US)

( * ) Notice: Subject to any disclaimer, the term of this patent is extended or adjusted under 35 U.S.C. 154(b) by 121 days.

(21) Appl. No.: 14/355,903

(22) PCT Filed: Nov. 9, 2012

(86) PCT No.: PCT/US2012/064269
§ 371 (c)(1),
(2) Date: May 2, 2014

(87) PCT Pub. No.: WO2013/070996
PCT Pub. Date: May 16, 2013

(65) Prior Publication Data
US 2014/0275136 A1 Sep. 18, 2014

Related U.S. Application Data

(60) Provisional application No. 61/558,619, filed on Nov. 11, 2011.

(51) Int. Cl.
*A61K 31/506* (2006.01)
(52) U.S. Cl.
CPC ................................. *A61K 31/506* (2013.01)
(58) Field of Classification Search
CPC ...................................................... A61K 31/506
See application file for complete search history.

(56) References Cited

U.S. PATENT DOCUMENTS

| | | | |
|---|---|---|---|
| 5,717,100 | A | 2/1998 | Selnick et al. |
| 6,037,136 | A | 3/2000 | Beach et al. |
| 6,204,467 | B1 | 3/2001 | Greenholtz, Jr. et al. |
| 6,268,391 | B1 | 7/2001 | Dickerson et al. |
| 6,358,932 | B1 | 3/2002 | Monia et al. |
| 6,391,636 | B1 | 5/2002 | Monia et al. |
| 6,458,813 | B1 | 10/2002 | Mantlo et al. |
| 6,911,446 | B2 | 6/2005 | Tang et al. |
| 7,482,367 | B2 | 1/2009 | Alkawa et al. |
| 8,501,758 | B2 | 8/2013 | Huang et al. |
| 8,541,575 | B2 | 9/2013 | Pulici et al. |
| 8,791,265 | B2 | 7/2014 | Pulici et al. |
| 8,946,250 | B2 | 2/2015 | Pulici et al. |
| 9,114,137 | B2 | 8/2015 | Pulici et al. |
| 9,387,208 | B2 | 7/2016 | Verma et al. |
| 9,593,099 | B2 | 3/2017 | Huang et al. |
| 9,593,100 | B2 | 3/2017 | Huang et al. |
| 9,763,941 | B2 | 9/2017 | Verma et al. |
| 2001/0006974 | A1 | 7/2001 | Byrd et al. |
| 2002/0137774 | A1 | 9/2002 | Riedl et al. |
| 2007/0099856 | A1* | 5/2007 | Gumerlock .......... A61K 31/517 514/34 |
| 2008/0085902 | A1 | 4/2008 | Bold |
| 2010/0022543 | A1 | 1/2010 | Melvin |
| 2010/0098763 | A1 | 4/2010 | Bechtold |
| 2010/0311751 | A1 | 12/2010 | Schmitt |
| 2011/0046370 | A1 | 2/2011 | Sim et al. |
| 2013/0053419 | A1 | 2/2013 | Pulici et al. |
| 2013/0217715 | A1 | 8/2013 | Pulici et al. |
| 2013/0296318 | A1 | 11/2013 | Huang et al. |
| 2014/0005150 | A1 | 1/2014 | Pulici et al. |
| 2015/0283136 | A1 | 10/2015 | Gallagher et al. |
| 2016/0263113 | A1 | 9/2016 | Huang et al. |
| 2016/0279129 | A1 | 9/2016 | Verma et al. |
| 2016/0280686 | A1 | 9/2016 | Huang et al. |
| 2016/0280687 | A1 | 9/2016 | Huang et al. |
| 2017/0202837 | A1 | 7/2017 | Verma et al. |

FOREIGN PATENT DOCUMENTS

| | | |
|---|---|---|
| EP | 2018851 | 1/2009 |
| EP | 2491923 | 8/2012 |
| JP | 2009-504796 | 2/2009 |
| JP | 2010-533711 | 10/2010 |
| JP | A 2011-515371 | 5/2011 |
| JP | A 2011-528698 | 11/2011 |
| JP | A 2012-512837 | 6/2012 |
| JP | A 2012-530099 | 11/2012 |
| JP | A 2013-503139 | 1/2013 |
| JP | 5475888 | 4/2014 |
| RU | 2402602 C1 | 10/2010 |
| WO | WO 1998/52940 | 11/1998 |

(Continued)

OTHER PUBLICATIONS

Flaherty et al., Nature Reviews |Drug Discovery; vol. 10, Nov. 2011 (Published online Oct. 31, 2011, http://www.nature.com/nrd/journal/v10/n11/full/nrd3579.html.*
Nicola Pizzolato et al: "Stochastic dynamics of leukemic cells under an intermittent targeted therapy", Theory in Biosciences, Springer-Verlag, Berlin/Heidelberg, vol. 138, No. 3, Apr. 9, 2811 (2811-84-89) pp. 283-218.*
Flaherty et al., Cancer 2010;116:4902-13.*
Haura et al., Clin Cancer Res. 16(8) Apr. 15, 2010, p. 2450-2451.*
Nature Reviews Drug Discovery, vol. 10, published online Oct. 31, 2011, pp. 811-812.*
Nicola Pizzolato et al., Stochastic dynamics of leukemic cells under an intermittent targeted therapy, Theory in Biosciences, vol. 130, No. 3, pp. 203-210, 2011.

(Continued)

*Primary Examiner* — Yong S. Chong
(74) *Attorney, Agent, or Firm* — Banner & Witcoff, Ltd.

(57) ABSTRACT

The present invention relates to a method of treating a patient with a serine/threonine kinase inhibitor wherein resistance to the treatment with a serine/threonine kinase inhibitor is suppressed by administering the serine/threonine kinase inhibitor on an intermittent dosing schedule.

32 Claims, 1 Drawing Sheet

(56) References Cited

FOREIGN PATENT DOCUMENTS

| WO | WO 2000/31063 | 6/2000 |
| WO | WO 2002/22577 | 3/2002 |
| WO | WO 03035047 | 5/2003 |
| WO | WO 2003/055860 | 7/2003 |
| WO | WO 2005/047266 | 5/2005 |
| WO | WO 2005/068452 | 7/2005 |
| WO | WO 2005/123719 | 12/2005 |
| WO | WO 2006/102079 | 9/2006 |
| WO | WO 2007/021966 | 2/2007 |
| WO | WO 2007/022956 | 3/2007 |
| WO | WO 2007/024843 | 3/2007 |
| WO | WO 2007/105058 | 9/2007 |
| WO | WO 2007/115286 | 10/2007 |
| WO | WO 2007/123892 | 11/2007 |
| WO | WO 2008/042639 | 4/2008 |
| WO | WO 2008/045627 | 4/2008 |
| WO | WO 2009/016460 | 2/2009 |
| WO | WO 2009/050291 | 4/2009 |
| WO | WO 2009/062676 | 5/2009 |
| WO | WO 2009/115572 | 9/2009 |
| WO | WO 2009/137391 | 11/2009 |
| WO | WO 2010/010154 | 1/2010 |
| WO | WO 2010/034838 | 4/2010 |
| WO | WO 2010/056662 | 5/2010 |
| WO | WO 2010/088336 | 8/2010 |
| WO | WO 2010/100127 | 9/2010 |
| WO | 2011/025927 A1 | 3/2011 |
| WO | WO 2011025927 A1 * | 3/2011 |
| WO | WO 2011/092088 | 8/2011 |
| WO | WO 2011/126903 | 10/2011 |
| WO | WO 2012/128709 | 9/2012 |
| WO | WO 2012/174061 | 12/2012 |

OTHER PUBLICATIONS

Das Thakur et al. (Feb. 14, 2013) "Modelling vemurafenib resistance in melanoma reveals a strategy to forestall drug resistance," Nature. 494:251-256—with Supplementary Information.

Das Thakur et al. (Oct. 4, 2013) "The evolution of Melanoma Resistance Reveals Therapeutic Opportunities," Cancer Research. 73:6106-6110.

Tomasetti et al. (2010) "An Elementary Approach to Modeling Drug Resistance in Cancer," Mathematical Biosciences and Engineering. 7(4):905-918.

Trinh et al. (2014) "Treatment of BRAF-mutated advanced cutaneous melanoma," Chinese Clinical Oncology. 3 (3):28-40.

Wang et al. (2011) "High dose intermittent sorafenib shows improved efficacy over conventional continuous dose in renal cell carcinoma," Journal of Translational Medicine. 9(1):220.

International Preliminary Report on Patentability corresponding to International Patent Application No. PCT/US2012/064269, issued May 13, 2014.

International Search Report with Written Opinion corresponding to International Patent Application No. PCT/US2012/064269, mailed Mar. 1, 2013.

Zhang et al. (2011) "Resistance of renal cell carcinoma to sorafenib is mediated by potentially reversible gene expression," PLoS One. 6(4):e19144. pp. 1-10.

"A Study of ARRY-438162 in Patients with Rheumatoid Arthritis," ClinicalTrials.gov, last updated Aug. 29, 2012, retrieved on Apr. 12, 2014, http://www.clinicaltrials.gov/2/show/NCT00650767?term=Arthritis&recr=Open, 3 pages.

"MEK Inhibitor MSC1936369B Plus FOLFIRI in Second Line K-Ras Mutated Metastatic Colorectal Cancer (mCRC)," ClinicalTrials.gov, last updated Oct. 21, 2013, retrived on Apr. 12, 2014, http://cliicaltrials.gov/2/show/NCT01085331?term-MSC1936369B&rank=1, 4 pages.

Arnold, "Synthetische Reaktionen Von dimethylformamid XVL* Formylierung Von y-Picolin," Coll. Czech. Chem. Commun., 1963, 28:863 (English Abstract).

CAS Registry No. 606143-89-9, "Substance Name: Binimetinib [USAN:INN]," [retrieved on Jun. 14, 2017]. Retrieved from the Internet: URL<https://chem.nlm.nih.gov/chemidplus/rn/606143-89-9>. 2 pages.

Cohen et al., "BRAF Mutation in Papillary Thyroid Carcinoma," J. Natl. Cancer Inst., 2003, 95:625-627.

Cohen, "The development and therapeutic potential of protein kinase inhibitors," Current Opinion in Chemical Biology, 1999, 3:459-465.

Culbertson et al., "New 7-substituted quinolone antibacterial agents. The synthesis of 1-ethyl-I,4-dihydro-4- oxo-7-(2-thiazolyl and 4-thiazolyl)-3-quinolinecarboxylic acids," J. Heterocycl. Chem, 1987, 24:1509.

Davies et al., "Mutations of the BRAF Gene in Human Cancer," Nature, 2002, 417:949-954.

Dhirendra et al., "Solid dispersions: A review," Pak. J. Pharm Sci, Apr. 2009, 22(2):234-246.

Fremin and Meloche, "From basic research to clinical development of MEK 1/2 inhibitors for cancer therapy," J. Hematology and Oncology, 2010, 3:8.

Goodacre et al., "Imidazo[1,2-a]pyrimidines as Functionally Selective and Orally Bioavailable GABAxA[alpha[2/ [alpha]3 binding Site Agonists for the Treatment of Anxiety Disorders," J. Med. Chem., 2006, 49(1):35-38.

Grimm et al., "A New Strategy for the Synthesis of Benzylic Sulfonamides: Palladium-Catalyzed Acylation and Sulfonamide Metathesis," J. Org. Chem, 2007, 72(21):8135-8138.

Hagemann and Rapp, "Isotope-specific functions of Raf kinases," Expt. Cell Res., 1999, 253:34-46.

Hingorani et al., "Suppression of BRAFV599E in Human Melanoma Abrogates Transformation," Cancer Res., 2003, 63:5198-520.

Hoshino et al., "Constitutive activation of the 41-/43-kDa mitogen-activated protein kinase signaling pathway in human tumors," Oncogene, 1999, 18:813-822.

International Preliminary Report on Patentability in International Application No. PCT/EP2009/0595506, dated Jan. 25, 2011, 6 pages.

International Preliminary Report on Patentability in International Application No. PCT/EP2011/050654, dated Jul. 31, 2012, 6 pages.

International Preliminary Report on Patentability in International Application No. PCT/EP2013/073452, dated May 12, 2015, 7 pages.

International Preliminary Report on Patentability in International Application No. PCT/US2010/046930, dated Feb. 28, 2012, 8 pages.

International Preliminary Report on Patentability in International Application No. PCT/US2012/066185, dated May 27, 2014, 8 pages.

International Preliminary Report on Patentability in International Application No. PCT/EP2011/063325, dated Feb. 5, 2013, 8 pages.

International Search Report and Written Opinion in International Application No. PCT/US2012/066185, dated Mar. 5, 2013, 13 pages.

International Search Report in International Application No. PCT/EP2009/059506, dated Sep. 23, 2009, 3 pages.

International Search Report in International Application No. PCT/EP2011/050654, dated Apr. 6, 2011, 4 pages.

International Search Report in International Application No. PCT/EP2011/063325, dated Aug. 31, 2011, 3 pages.

International Search Report in International Application No. PCT/EP2013/073452, dated Dec. 13, 2013, 5 pages.

International Search Report in International Application No. PCT/US2010/046930, dated Oct. 19, 2010, 5 pages.

Japanese Preliminary Examination Report in Japanese Application No. 2014-098022, dated Nov. 18, 2015, 5 pages (with English Translation).

Kolch et al., "The role of Raf kinases in malignant transformation," Exp. Rev. Mol. Med, http://citeseerx.ist.psu.edu/viewdoc/download?doi=10.1.1.114.8626&rep=rep1&type=pdf, Apr. 25, 2002,18 pages.

Korean Search Report for Application No. UAE/P/0202/2012, dated Mar. 10, 2017, 8 pages, English translation.

(56) References Cited

OTHER PUBLICATIONS

Lai et al., "Cotargeting histone deacetylases and oncongenic BRAF synergistically kills human melanoma cells by necrosis independently of RIPK1 and RIPK3," Cell Death and Disease, 2013, 4:e655, 13 pages.

Lai, Fritz et al., "Histone Deacetylases (HDACs) as Mediators of Resistance to Apoptosis in Melanoma and as Targets for Combination Therapy with Selective BRAF Inhibitors," Advances in Pharmacology, Sep. 6, 2012, vol. 65, p. 27-43.

McCubrey et al., "Emerging MEK inhibitors," Expert Opinion Emerging Drugs, Inform Healthcare, 2010, 15(2):203-223.

McLaughlin et al., "A Simple, Modular method for the Synthesis of 3,4,5-Trisubstituted Pyrazoles," JOC 2008, 73:4309-4312.

Mercer and Pritchard, "Raf proteins and cancer: B-Raf is identified as a mutational target," Biochim. Biophys. Acta, 2003, 1653:25-40.

Peyssonnaux and Eychene, "The Raf/MEK/ERK pathway: new concepts of activation," Biology of the Cell, 2001, 93:53-62.

Raju et al., "Inhibition of DNA Repair as a Mechanism of Enhanced Radioresponse of Head and Neck Carcinoma Cells by a Selective Cyclooxygenase-2 Inhibitor, Celecoxib," Int. J. Radiation Oncology Biol. Phys., 2005, 53:520-528.

Saulnier et al., "An Efficient method for the Synthesis of Guanidino Prodrugs," Bioorganic and Medicinal Chemistry Letters, 1994, 4:1985.

Sherman et al., "Biologically targeted therapies for thyroid cancers," Thyroid Cancer, Jan. 2011, 329-349.

Takeuchi, Hirofumi, "Strategy for pharmaceutical formulation and new technology," CMC publication, KK, Mar. 31, 2007, pp. 117, 212, 11 pages, with certified English translation.

Tannapfel et al., "Mutations of the BRAF gene in cholangiocardinoma but not the hepatocellular carcinoma," Gut, 2003, 52:706-712.

Tran et al., "Dissolution-modulating mechanism of pH modifiers in solid dispersion containing weakly acidic or basic drugs with poor water solubility," Expert. Opin. Drug Deliv., Dec. 2010, 7(5):647-661.

Trivedi et al., "Novel dihydropyrimidines as a potential new class of antitubercular agents," Bioorganic & medicinal Chemistry Letters, 2010, 20:6100-6102.

Velculescu, "Defining the Blueprint of the Cancer Genome," Carcinogenesis, 2008, 29:1087-1091.

Wellbrock et al., "B-RAF is an Oncogene in Melanocytes," Cancer Res., 2004, 64:2338-2342.

Wojnowski et al., "Endothelial apoptosis in Braf-deficient mice," Nature Genet., 1997, 16:293-297.

Written Opinion in International Application No. PCT/EP2013/073452, dated Dec. 13, 2013, 6 pages.

Written Opinion of the International Searching Authority in International Application No. PCT/EP2009/0595506, dated Sep. 23, 2009, 5 pages.

Written Opinion of the International Searching Authority in International Application No. PCT/EP2011/050654, dated Apr. 6, 2011, 5 pages.

Written Opinion of the International Searching Authority in International Application No. PCT/EP2011/063325, dated Feb. 3, 2013, 6 pages.

Written Opinion of the International Searching Authority in International Application No. PCT/US2010/046930, dated Oct. 9, 2010, 7 pages.

Young et al., "Discovery and evaluation of potent P1 aryl heterocycle-based thrombin inhibitors," J. Med. Chem., 2004. 47:2995-3008.

* cited by examiner

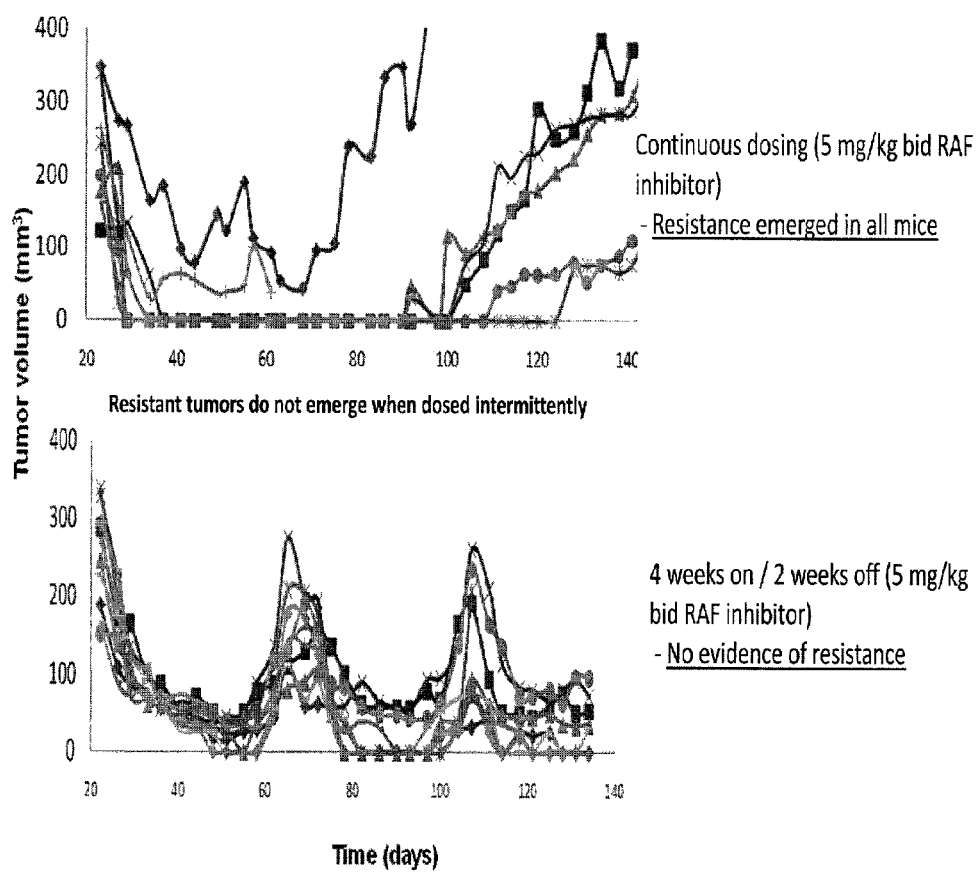

METHOD OF TREATING A PROLIFERATIVE DISEASE

SUMMARY

The present invention relates to a method of suppressing resistance to treatment with inhibitors of BRAF.

BACKGROUND

The involvement of kinases in proliferative diseases is well known. For example, kinases associated with tumorigenesis include the receptor tyrosine kinases and the serine/threonine kinase, Raf kinase. These kinases play critical roles in signal transduction pathways that influence and regulate many cellular functions such as proliferation, differentiation, and survival.

The development of therapies for the treatment of proliferative diseases remains a formidable challenge. A continuing need exists for improved therapeutic methods, particularly in view of the many variations amongst cancer cells with respect to their underlying mechanisms of growth and survival, their response to therapeutic agents, and their ability to mutate and become refractory or resistant to such agents.

Raf kinase is part of the Mitogen-Activated Protein Kinase (MAPK) signaling pathway comprising the Ras-Raf-MEK1-ERK signaling molecules. Raf has three distinct isoforms A-Raf, B-Raf, and C-Raf as distinguished by their ability to interact with its upstream modulator Ras. An activating mutation of one of the Ras genes can be seen in about 20% of all tumors and the Ras/Raf/MEK/ERK pathway is activated in about 30% of all tumors (Bos et al., Cancer Res. 49:4682-4689, 1989; Hoshino et al., Oncogene 18:813-822, 1999). Activating mutation in the kinase domain of B-Raf occurs in about 66% of melanomas, 12% of colon carcinoma and 14% of liver cancer (Davies et al., Nature 417:949-954, 2002; Yuen et al., Cancer Research 62:6451-6455, 2002; Brose et al., Cancer Research 62:6997-7000, 2002).

Small molecule RAF inhibitors, such as vemurafenib, have demonstrated proof-of-concept that BRAFV600E is a key driver of proliferation and survival in melanoma, as evidenced by tumor regression and prolonged survival in patients in late stage clinical trials. Unfortunately, the tumor response can be short-lived when resistance to a RAF inhibitor rapidly develops.

BRIEF DESCRIPTION OF THE DRAWINGS

FIG. 1 Comparison of continuous and intermittent dosing of a BRAF inhibitor of formula II shows that taking away a growth advantage for the resistant cells by intermittent dosing delays or prevents the onset of resistance to the BRAF inhibitor.

DETAILED DESCRIPTION

The present invention is based on the discovery that Raf kinase resistant tumor cells are 'less fit' than tumor cells which are sensitive to the Raf kinase inhibitor and have a selective disadvantage over sensitive cells in the absence of the Raf kinase inhibitor. Thus, according to the present invention resistance to treatment with a Raf kinase inhibitor is suppressed by administering the Raf kinase inhibitor on an intermittent dosing schedule.

Suppressing resistance to treatment means delaying or preventing the onset of resistance to treatment with the Raf kinase inhibitor.

In this application, intermittent dosing schedule means that that the B-Raf kinase inhibitor is administered for a period of time followed by a period of time wherein treatment with the B-Raf kinase inhibitor is withheld. For example, the Raf kinase inhibitor is administered daily for a period of 4 weeks followed by a period of two weeks without treatment and the cycle is repeated while the patient is treated with the Raf kinase inhibitor.

BRAF inhibitors and their use for treating proliferative diseases are known in the art Vemurafenib (PLX4032) is a BRAF inhibitor which was approved by the FDA for the treatment of patients with melanoma whose tumors express the BRAF V600E mutation. Vemurafenib has the following chemical structure:

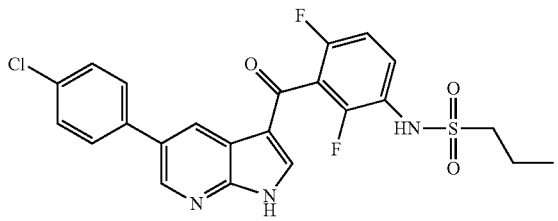 [SMILES: CCCS(=O)(=O)Nc1ccc(F)c(C(=O)c2c[nH]c3ncc(-c4ccc(Cl)cc4)cc23)c1F]

Another class of compounds that inhibits certain kinases in the MAPK pathway is the benzimidazolyl pyridyl ethers. U.S. Pat. No. 7,482,367, which is here incorporate by reference in its entirety, discloses a B-RAF kinase inhibitor for formula I.

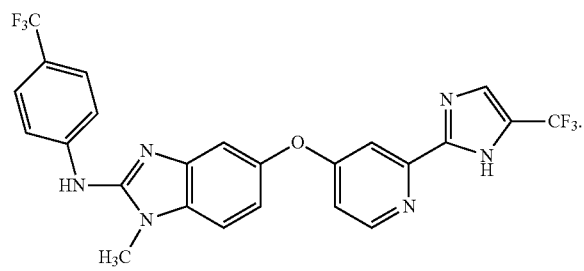

(I)

Another class of compounds that inhibits certain kinases in the MAPK pathway is the pyrrazole pyrimidines. WO 2011/025927, which is here incorporate by reference in its entirety, discloses the compound of formula II as an inhibitor of BRAF kinase, particularly with the BRAFV600E mutation:

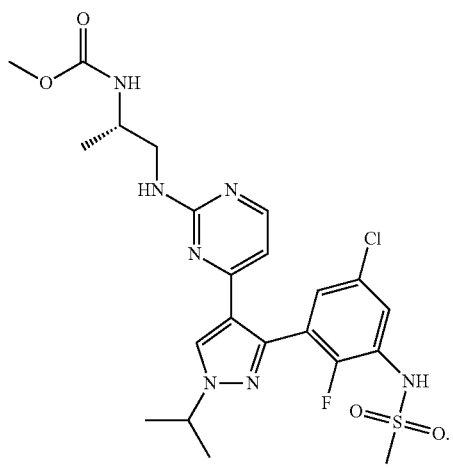

(II)

In the present method, the BRAF inhibitor is preferably a compound of formula II.

In an early passage primary human melanoma xenograft model designed to measure the emergence of resistance to a BRAF inhibitor, we have established that treatment of the xenografts with a BRAF inhibitor on a long term continuous dosing regimen at clinically relevant doses resulted in the appearance of resistant tumors over the course of 4 to 6 weeks. Pharmacodynamic (PD) analysis within individual tumors indicated that the RAF-MEK-ERK pathway is still suppressed in resistant tumors, although the degree and duration of suppression is less than in sensitive tumors. Furthermore, the kinetics of pathway inhibition and recovery are different between each resistant tumor. Biochemical analyses indicate that serine/threonine kinases and modulation of negative feedback loops to serine/threonine kinases may be involved in resistance, as well as up-regulation of BRAF V600E expression. Pharmacological evaluation of tumor response has provided insight into tumor cell populations and the evolution of resistance. Increasing the dose of drug administered to mice bearing resistant tumors leads to a significant yet transient tumor response, followed by tumor progression. Taken together with the PD data, it is reasonable to conclude that there is a great deal of tumor cell heterogeneity, and that tumors are able to rapidly adapt to the selective pressure being applied by administration of the drug. Further support for this conclusion was obtained by suspending drug treatment from mice implanted with resistant tumors. Upon drug withdrawal, tumors initially regressed for several days to weeks, followed by re-growth. These data indicate that the adaptation which occurs within a tumor cell population under selective pressure make the cells less fit in the absence of drug.

All resistant tumors have higher levels of p-ERK in the presence of the BRAF inhibitor compound compared to sensitive tumors and have faster recovery rates post-dose. The kinetics of the recovery vary between resistant tumors. BRAF resistant tumors depend on the presence of drug for growth and removal of the drug causes tumors to regress. Resistant cells are less fit then sensitive cells in the absence of compound. The present invention utilizes this discovery to suppress resistance to treatment with a BRAF inhibitor by administering the BRAF inhibitor on an intermittent dosing schedule Thus, the present invention includes a method of treating a proliferative disease, which comprises suppressing resistance to treatment with a BRAF kinase inhibitor by administering the BRAF kinase inhibitor on an intermittent dosing schedule.

In particular, the present invention includes A method of treating a proliferative disease characterized by a mutation in BRAF kinase, which comprises suppressing resistance to treatment with a BRAF inhibitor of the Formula II

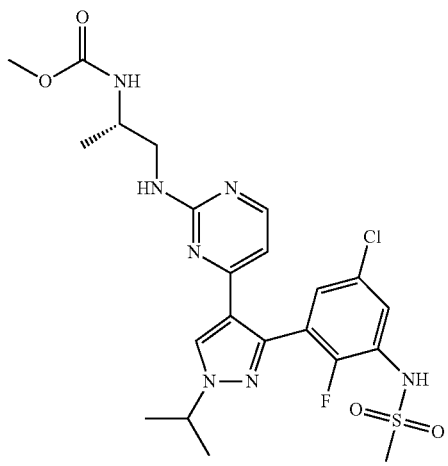

(II)

by administering the BRAF inhibitor of Formula II on an intermittent dosing schedule.

In a preferred embodiment, the present invention further relates to a method of treating a proliferative disease characterized by a mutation in BRAF kinase, which comprises suppressing resistance to treatment with a BRAF inhibitor by administering the BRAF inhibitor on an intermittent dosing schedule.

This aspect of the invention further relates to a method wherein the BRAF mutation is a V600 mutation, such as BRAFV600E.

The proliferative diseases treated by the inventive method include cancer such as, but not limited to, bladder, breast, brain, head and neck, liver, biliary tract, carcinomas, acute and chronic lymphoid leukemias, acute and chronic myelogenous leukemias, chronic myelomonocytic leukemias, colorectal, gastric, gastrointestinal stromal, glioma, lymphomas, melanomas, multiple myeloma, myeloproliferative diseases, neuroendocrine, lung, pancreatic, ovarian, prostate, renal cell, sarcomas and thyroid, such as papillary thyroid, cancers. Other proliferative diseases include mast cell leukemia, germ cell tumors, small-cell lung carcinoma, gastrointestinal stromal tumors, neuroblastoma, and osteosarcoma.

More particularly, the proliferative disease treated by the inventive method is melanoma which is characterized by a V600 mutation, such as BRAFV600E, or colorectal cancer characterized by a V600 mutation, such as BRAFV600E.

In an important aspect, the intermittent dosing schedule comprises administering the BRAF inhibitor for a period of 4 weeks followed by a period of two weeks without treatment and repeating the cycle while the patient is treated with the BRAF inhibitor or until resistance emerges. However, additional intermittent dosing schedules include, for example, cycles of 1 one week on 1 week off, 2 weeks on 1 or 2 weeks off, 3 weeks on 1, 2 or 3 weeks off, 4 weeks on 1, 2, 3 or 4 weeks off, especially 4 weeks on 1 week off or 4 weeks on 2 weeks off, 5 weeks on 1, 2 3, 4, or 5 weeks off, 6 weeks on and 1, 2, 3, 4, 5 or 6 weeks off, and so on.

This invention further includes use of a BRAF inhibitor for the preparation of a medicament for the treatment of a proliferative disease whereby the BRAF inhibitor is administered on an intermittent dosing schedule. In particular, use of a BRAF inhibitor of the Formula II for the preparation of a medicament for the treatment of a proliferative disease whereby the BRAF inhibitor of Formula II is administered on an intermittent dosing schedule The following Example illustrates the present invention.

EXAMPLE 1

Hmex1906 primary human melanoma tumors are implanted at passage 3 into nude mice. The mice were monitored until the implanted tumors reached 200-400 mm$^3$. Once this size is reached, the mice are dosed bid with 5 mg/kg of a Raf inhibitor (Compound of Formula II) for 4 weeks. Some of the mice continue treatment while others are subject to an intermittent treatment schedule of 4 weeks of treatment and 2 weeks of drug holiday.

The results are shown in FIG. 1. Resistance emerged in all mice receiving the Compound of Formula II on a continuous basis, but there is no evidence of resistance in the mice that were subject to an intermittent dosing schedule.

We claim:

1. A method of treating a proliferative disease in a subject in need thereof, wherein the proliferative disease is melanoma or colorectal cancer, and wherein the proliferative disease is characterized by a mutation in BRAF kinase, wherein the method comprises suppressing resistance to treatment with a BRAF inhibitor of the Formula II

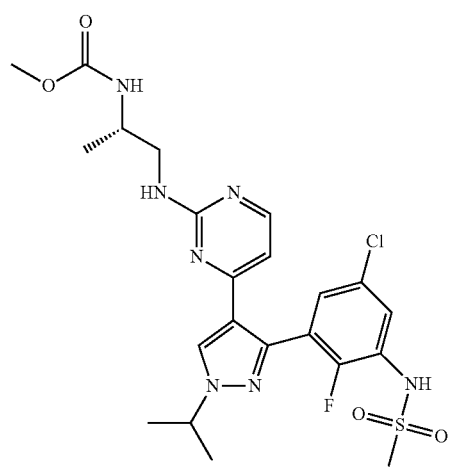

(II)

by administering the BRAF inhibitor of Formula II to the subject on an intermittent dosing schedule, wherein the intermittent dosing schedule comprises administering the BRAF inhibitor for a period of 1, 2, 3, 4, 5, or 6 weeks followed by a period of 1, 2, 3, 4, 5, or 6 weeks without treatment.

2. A method of claim 1 wherein the BRAF mutation is a V600 mutation.

3. A method of claim 1 wherein the proliferative disease is melanoma which is characterized by a V600 mutation or colorectal cancer characterized by a V600 mutation.

4. A method of claim 1 wherein the proliferative disease is melanoma which is characterized by BRAFV600E or colorectal cancer characterized by BRAFV600E.

5. A method of claim 1 wherein the intermittent dosing schedule comprises administering the BRAF inhibitor for a period of 4 weeks followed by a period of two weeks without treatment and repeating the cycle while the patient is treated with the BRAF inhibitor or until resistance emerges.

6. A method of claim 1 wherein the intermittent dosing schedule improves a therapeutic effect in tumor cells already resistant to treatment with the BRAF kinase inhibitor of Formula II.

7. The method of claim 1, wherein the proliferative disease is a tumor.

8. The method of claim 7, wherein said tumor is melanoma which is characterized by a V600 mutation.

9. The method of claim 8, wherein said tumor is melanoma which is characterized by a V600E mutation.

10. The method of claim 8, wherein the BRAF inhibitor of Fomula II is administered once daily during the period of administration of the BRAF inhibitor of Formula II.

11. The method of claim 9, wherein the BRAF inhibitor of Formula II is administered once daily during the period of administration of the BRAF inhibitor of Formula II.

12. The method of claim 11, wherein the intermittent dosing schedule comprises administering the BRAF inhibitor of Formula II for a period of 4 weeks followed by a period of 2 weeks wherein treatment with the BRAF inhibitor of Formula II is withheld, and repeating the cycle while the patient is treated with the BRAF inhibitor of Formula II.

13. The method of claim 11, wherein the intermittent dosing schedule comprises administering the BRAF inhibitor for a period of 1 week followed by a period of 1 week wherein treatment with the BRAF inhibitor of Formula II is withheld and repeating the cycle while the patient is treated with the BRAF inhibitor.

14. The method of claim 11, wherein the intermittent dosing schedule comprises administering the BRAF inhibitor for a period of 2 weeks followed by a period of 1 week wherein treatment with the BRAF inhibitor of Formula II is withheld and repeating the cycle while the patient is treated with the BRAF inhibitor.

15. The method of claim 11, wherein the intermittent dosing schedule comprises administering the BRAF inhibitor for a period of 2 weeks followed by a period of 2 weeks wherein treatment with the BRAF inhibitor of Formula II is withheld and repeating the cycle while the patient is treated with the BRAF inhibitor.

16. The method of claim 11, wherein the intermittent dosing schedule comprises administering the BRAF inhibitor for a period of 3 weeks followed by a period of 1 week wherein treatment with the BRAF inhibitor of Formula II is withheld and repeating the cycle while the patient is treated with the BRAF inhibitor.

17. The method of claim 11, wherein the intermittent dosing schedule comprises administering the BRAF inhibitor for a period of 3 weeks followed by a period of 2 weeks wherein treatment with the BRAF inhibitor of Formula II is withheld and repeating the cycle while the patient is treated with the BRAF inhibitor.

18. The method of claim 11, wherein the intermittent dosing schedule comprises administering the BRAF inhibitor for a period of 3 weeks followed by a period of 3 weeks wherein treatment with the BRAF inhibitor of Formula II is withheld and repeating the cycle while the patient is treated with the BRAF inhibitor.

19. The method of claim 11, wherein the intermittent dosing schedule comprises administering the BRAF inhibitor for a period of 4 weeks followed by a period of 1 week wherein treatment with the BRAF inhibitor of Formula II is withheld and repeating the cycle while the patient is treated with the BRAF inhibitor.

20. The method of claim 11, wherein the intermittent dosing schedule comprises administering the BRAF inhibitor for a period of 4 weeks followed by a period of 3 weeks wherein treatment with the BRAF inhibitor of Formula II is withheld and repeating the cycle while the patient is treated with the BRAF inhibitor.

21. The method of claim 11, wherein the intermittent dosing schedule comprises administering the BRAF inhibitor for a period of 4 weeks followed by a period of 4 weeks wherein treatment with the BRAF inhibitor of Formula II is withheld and repeating the cycle while the patient is treated with the BRAF inhibitor.

22. The method of claim 11, wherein the intermittent dosing schedule comprises administering the BRAF inhibitor for a period of 5 weeks followed by a period of 1 week wherein treatment with the BRAF inhibitor of Formula II is withheld and repeating the cycle while the patient is treated with the BRAF inhibitor.

23. The method of claim 11, wherein the intermittent dosing schedule comprises administering the BRAF inhibitor for a period of 5 weeks followed by a period of 2 weeks wherein treatment with the BRAF inhibitor of Formula II is withheld and repeating the cycle while the patient is treated with the BRAF inhibitor.

24. The method of claim 11, wherein the intermittent dosing schedule comprises administering the BRAF inhibitor for a period of 5 weeks followed by a period of 3 weeks wherein treatment with the BRAF inhibitor of Formula II is withheld and repeating the cycle while the patient is treated with the BRAF inhibitor.

25. The method of claim 11, wherein the intermittent dosing schedule comprises administering the BRAF inhibitor for a period of 5 weeks followed by a period of 4 weeks wherein treatment with the BRAF inhibitor of Formula II is withheld and repeating the cycle while the patient is treated with the BRAF inhibitor.

26. The method of claim 11, wherein the intermittent dosing schedule comprises administering the BRAF inhibitor for a period of 5 weeks followed by a period of 5 weeks wherein treatment with the BRAF inhibitor of Formula II is withheld and repeating the cycle while the patient is treated with the BRAF inhibitor.

27. The method of claim 11, wherein the intermittent dosing schedule comprises administering the BRAF inhibitor for a period of 6 weeks followed by a period of 1 week wherein treatment with the BRAF inhibitor of Formula II is withheld and repeating the cycle while the patient is treated with the BRAF inhibitor.

28. The method of claim 11, wherein the intermittent dosing schedule comprises administering the BRAF inhibitor for a period of 6 weeks followed by a period of 2 weeks wherein treatment with the BRAF inhibitor of Formula II is withheld and repeating the cycle while the patient is treated with the BRAF inhibitor.

29. The method of claim 11, wherein the intermittent dosing schedule comprises administering the BRAF inhibitor for a period of 6 weeks followed by a period of 3 weeks wherein treatment with the BRAF inhibitor of Formula II is withheld and repeating the cycle while the patient is treated with the BRAF inhibitor.

30. The method of claim 11, wherein the intermittent dosing schedule comprises administering the BRAF inhibitor for a period of 6 weeks followed by a period of 4 weeks wherein treatment with the BRAF inhibitor of Formula II is withheld and repeating the cycle while the patient is treated with the BRAF inhibitor.

31. The method of claim 11, wherein the intermittent dosing schedule comprises administering the BRAF inhibitor for a period of 6 weeks followed by a period of 5 weeks wherein treatment with the BRAF inhibitor of Formula II is withheld and repeating the cycle while the patient is treated with the BRAF inhibitor.

32. The method of claim 11, wherein the intermittent dosing schedule comprises administering the BRAF inhibitor for a period of 6 weeks followed by a period of 6 weeks wherein treatment with the BRAF inhibitor of Formula II is withheld and repeating the cycle while the patient is treated with the BRAF inhibitor.

\* \* \* \* \*